United States Patent [19]

Beaulieu et al.

[11] Patent Number: 5,028,732
[45] Date of Patent: Jul. 2, 1991

[54] HERBICIDALLY ACTIVE AMINO DIPHENYL ETHERS

[75] Inventors: Ann H. Beaulieu, Gwynedd; Roy Y. Yih, Doylestown, both of Pa.

[73] Assignee: Rohm and Haas Company, Philadelphia, Pa.

[21] Appl. No.: 840,978

[22] Filed: Mar. 13, 1986

Related U.S. Application Data

[63] Continuation of Ser. No. 507,261, Jun. 23, 1983, abandoned.

[51] Int. Cl.$^5$ ............................................. C07C 205/00
[52] U.S. Cl. ........................................ 560/21; 560/47; 546/286; 546/288; 546/302; 558/232; 558/252; 564/79; 564/80; 564/163; 564/166; 564/167; 71/111
[58] Field of Search ................. 560/21, 47; 546/286, 546/288, 30; 558/232, 252; 564/167; 71/111

[56] References Cited

U.S. PATENT DOCUMENTS

| | | | |
|---|---|---|---|
| 3,137,563 | 6/1964 | Newcomer | 71/2.6 |
| 3,282,991 | 11/1966 | Klein | 71/2.6 |
| 3,325,274 | 6/1967 | Anderson | 71/2.6 |
| 4,039,588 | 8/1977 | Wilson et al. | |
| 4,063,929 | 12/1977 | Bayer et al. | 560/21 |
| 4,277,624 | 7/1981 | Yoshimoto et al. | 568/586 |

FOREIGN PATENT DOCUMENTS 0072348 2/1983 European Pat. Off.

OTHER PUBLICATIONS

Central Patents Index, Section C: Agdoc 09317 C/06 (DS 2960-829), Derwent Publications Ltd. (1980).
Central Patents Index, Section C: Agdoc 48893 E/24 (J57072947), Derwent Publications Ltd. (1982).
Central Patents Index, Section C: Agdoc 48892 E/24 (J577072946), Derwent Publications Ltd. (1982).

Primary Examiner—Paul J. Killos
Attorney, Agent, or Firm—Polly E. Ramstad; Barbara V. Maurer

[57] ABSTRACT

Compounds having the formula

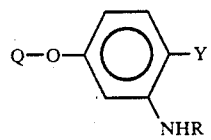

(I)

wherein Q is substituted phenyl or substituted pyridyl; Y is nitro, cyano, or halogen; R is a group of the formula —(CHR$^1$)$_m$—A—(CH$^2$)—$_n$—R$^3$ wherein R$^1$ and R$^2$, independently of each other and in each (CHR$^1$) and (CHR$^2$) group, are hydrogen, unsubstituted or substituted alkyl, alkoxy, or alkylthio; A is —N(R$^1$)—, —N(O)—, —O—, —S—, —S(O)—, —S(O)$_2$—, —C(O)—, —C(O)B—, or —N(H)S(O)$_2$—; B is alkylene, —O—, —S—, or —N(R$^4$)—; R$^3$ is cyano, halogen, or C(O)Z; R$^4$ is hydrogen or unsubstituted or substituted alkyl; Z is hydrogen, unsubstituted or substituted alkyl, —N(R$^4$)$_2$, —OR$^5$, —SR$^5$, or —N(R$^4$)SO$_2$R$^6$; R$^5$ is hydrogen, unsubstituted or substituted alkyl, or an agronomically-acceptable cation; R$^6$ is alkyl, unsubstituted or substituted phenyl, or hydroxy or its agronomically-acceptable salts; m is an integer from 2 to 10; and n is an integer from 1 to 3, are herbicidally active.

19 Claims, No Drawings

HERBICIDALLY ACTIVE AMINO DIPHENYL ETHERS

This application is a continuation of application Ser. No. 507,261, filed June 23, 1983.

BACKGROUND OF THE INVENTION

1. Field of the Invention

This invention relates to novel N-substituted amino diphenyl ethers, to compositions containing the N-substituted amino diphenyl ethers, and to methods of controlling weeds by the use of the N-substituted amino diphenyl ethers.

2. Description of the Prior Art

Wilson et al, U.S. Pat. No. 4,039,588, discloses amino-substituted diphenyl ethers, such as 2,4-dichloro-3'-dimethylamino-4'-nitrodiphenyl ether and 2,4-dichloro-3'-isopropylamino-4'-nitrodiphenyl ether.

Japanese Patent Publication No. 72946, published May 7, 1982, discloses amino diphenyl ether derivatives, such as 2-chloro-4-trifluoromethyl-3'-amino-4'nitrodiphenyl ether, in which one of the two free nitrogen electrons participates in a covalent bond with a hydrogen atom, a lower alkyl group, a lower alkenyl group, or a lower alkynyl group, and the other free electron participates in a covalent bond with an alkoxycarbonylalkyl group.

German Patent 2960829, published Mar. 12, 1981, discloses 2-chloro-6-nitro-3-(phenoxy or phenylthio)aniline plant growth regulants and herbicides, wherein one of the two free aniline nitrogen electrons is bonded to nitrogen, alkyl, cycloalkyl, chloro- or hydroxy-substituted alkyl, allyl or trifluoroacetyl, and the other free aniline nitrogen electron is bonded to hydrogen, methyl, ethyl, n-propyl, or isopropyl, or the two free aniline nitrogen electrons may be bonded to an alkylene group having up to five members, optionally interrupted by O, NH, NCH$_3$ or CH—N(CH$_3$)$_2$.

German Patent Application DE2938595, published Apr. 23, 1981, discloses a process for producing 2- or 4-chloro-3-phenoxy-6-nitro-N-substituted anilines, wherein the N-substituent can be hydrogen, alkyl, alkenyl, alkynyl, hydroxy, alkoxy, phenoxy, halophenoxy, alkylphenoxy, alkoxyphenoxy, nitrophenoxy, cyanophenoxy, amino, alkylthio, benzyl, alkoxycarbonylalkyl, aminocarbonylalkyl, and the like.

German Patent Application DE2926829 discloses 2-chloro-4-trifluoromethylphenyl-3'-nitrophenyl ethers having in the 4'-position a hydrogen atom or a nitro group, and 2-chloro-4-trifluoromethylphenyl-4'-nitrophenyl ethers having in the 3'-position a nitro, alkoxy, alkylthio, hydroxy, sulfhydryl, amino, and monoalkylamino. U.S. Pat. No. 4,277,624, issued July 7, 1981, corresponds to German Patent Application DE2926829.

European Patent Application 72348, published Feb. 16, 1983, discloses N-substituted and N,N-disubstituted-3-amino-4-nitrodiphenyl ethers and their use as herbicides.

DESCRIPTION OF THE INVENTION

The compounds of the present invention are characterized in that, when (1) the chain length between the nitrodiphenyl ether 3'-position nitrogen atom and the chain terminal group is from 4 to 14 atoms, (2) the chain is interrupted and linked by a heteroatom or heteroatom containing functional group, for example, O, S, S(O), S(O)$_2$, C(O), and the like, and (3) the terminal group is cyano, halo, carboxy or salt thereof, alkylcarbonyl, alkoxycarbonyl, alkylthiocarbonyl, aminocarbonyl, alkylaminocarbonyl, dialkylaminocarbonyl, or alkylsulfonamido, or a substituted derivative thereof, the resulting compounds possess high selectivity and herbicidal efficacy.

In accordance with the present invention there is provided a new class of diphenyl ethers having the formula

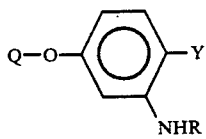

wherein:

Q is a group of the formula

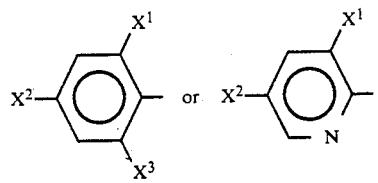

$X^1$ is a hydrogen atom, a cyano group, or a halogen atom, preferably a halogen atom and most preferably a chlorine atom;

$X^2$ is a haloalkyl group, preferably a trifluoromethyl group, or a halogen atom;

$X^3$ is a hydrogen atom or a halogen atom;

Y is a nitro group, a cyano group, or a halogen atom;

R is a group of the formula

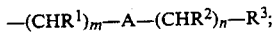

$R^1$ and $R^2$, independently of each other and in each (CHR$^1$) and (CHR$^2$) group, are a hydrogen atom; an unsubstituted or substituted straight- or branched-chain (C$_1$–C$_6$) alkyl group; a (C$_1$–C$_6$) alkoxy group; or a (C$_1$–C$_6$) alkylthio group; provided that $R^1$ and $R^2$ may not be alkoxy or alkylthio alpha to an -NH-moiety;

A is —N(R$^1$)—, —N(O)—, —O—, —S—, —S(O)—, —S(O)$_2$—, —C(O)—, —C(O)B—, or —N(H)S(O)$_2$—;

B is a straight- or branched-chain (C$_1$–C$_6$) alkylene group, —O—, —S—, or —N(R$^4$)—;

$R^3$ is a cyano group, a halogen atom, preferably chlorine or bromine, or a group of the formula

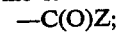

$R^4$ is a hydrogen atom or an unsubstituted or substituted straight- or branched-chain (C$_1$–C$_6$) alkyl group;

Z is a hydrogen atom; an unsubstituted or substituted straight- or branched-chain (C$_1$–C$_6$) alkyl group; —N(R$^4$)$_2$; —OR$^5$; —SR$^5$; or —N(R$^4$)SO$_2$R$^6$;

$R^5$ is a hydrogen atom; an unsubstituted or substituted straight- or branched-chain (C$_1$–C$_6$) alkyl group; or an agronomically-acceptable cation, preferably an alkali metal, alkaline earth metal, ammonium, substituted ammonium, sulfonium, substituted sulfonium, sulfoxonium, or substituted sulfoxonium cation;

$R^6$ is an unsubstituted straight- or branched-chain (C$_1$–C$_6$) alkyl group; an unsubstituted or substituted phenyl group with up to three substituents which can be the same or different and are selected from chlorine, bromine, fluorine ($C_1$–$C_6$)alkoxy and ($C_1$–$C_6$) alkyl which can be straight- or branched-chain and unsubstituted or substituted with up to three substituents which can be the same or different and are selected from chlorine, bromine, and ($C_1$–$C_6$) alkoxy; or a hydroxy group and its agronomically-acceptable salts;

m is an integer from 2 to 10; and n is an integer from 1 to 3.

When $R^1$, $R^2$, $R^4$, or $R^5$ is a substituted alkyl group, there can be up to three substituents which can be the same or different. Preferably, the substituents will be selected from chlorine, bromine, fluorine, hydroxy, ($C_1$–$C_6$) alkoxy, ($C_1$–$C_6$) alkylthio, ($C_1$–$C_6$) alkylcarbonyl, ($C_1$–$C_6$) alkoxycarbonyl, amino, mono- or di-($C_1$–$C_6$) alkylamino, ($C_1$–$C_6$) alkylcarbonyloxy and unsubstituted or substituted phenyl, phenoxy, or phenylthio having up to three substituents which can be the same or different and preferably will be selected from chlorine, bromine, fluorine, hydroxy, ($C_1$–$C_6$)alkoxy, ($C_1$–$C_6$)alkylthio, and ($C_1$–$C_6$)alkyl unsubstituted or substituted with up to three substituents which can be the same or different and preferably are selected from chlorine, bromine, fluorine, hydroxy and $C_1$–$C_6$ alkoxy.

Among the agronomically-acceptable salts are those in which the agronomically-acceptable cation is an alkali metal cation, such as sodium or potassium, or an alkaline earth metal cation, such as calcium, magnesium, barium, or strontium, an ammonium cation, such as those having the formula $NZ^1Z^2Z^3Z^4$, wherein each of $Z^1$, $Z^2$, $Z^3$, and $Z^4$ is individually a hydrogen atom, a hydroxy group, a ($C_1$–$C_4$)alkoxy group, a ($C_1$–$C_{20}$)alkyl group, a ($C_3$–$C_8$)alkenyl group, a ($C_3$–$C_8$) alkynyl group, a ($C_2$–$C_8$)hydroxyalkyl group, a ($C_2$–$C_8$) alkoxyalkyl group, a ($C_2$–$C_6$)aminoalkyl group, a ($C_2$–$C_6$) haloalkyl group, a substituted or unsubstituted phenyl group, a substituted or unsubstituted phenylalkyl group, having up to 4 carbon atoms in the alkyl moiety, or any two of $Z^1$, $Z^2$, $Z^3$, or $Z^4$ can be taken together to form with the nitrogen atom a 5- or 6-member heterocyclic ring, optionally having up to one additional hetero oxygen, nitrogen, or sulfur atom in the ring, and preferably saturated, such as a piperidine, morpholino, pyrrolidino, or piperazino ring, or the like, or any three of $Z^1$, $Z^2$, $Z^3$, or $Z^4$ can be taken together to form with the nitrogen atom a 5- or 6-member aromatic heterocyclic ring, such as a piperazole or pyridine ring. When the ammonium group contains a substituted phenyl or substituted phenylalkyl group, the substituents will generally be selected from halogen atoms, ($C_1$–$C_8$)alkyl groups, ($C_1$–$C_4$)alkoxy groups, hydroxy groups, nitro groups, trifluoromethyl groups, cyano groups, amino groups and ($C_1$–$C_4$) alkylthio groups. Such substituted phenyl groups preferably have up to two such substituents. Representative ammonium cations include ammonium, dimethylammonium, 2-ethylhexylammonium, bis(2-hydroxyethyl)ammonium, tris(2-hydroxyethyl)ammonium, dicyclohexylammonium, t-octylammonium, 2-hydroxyethylammonium, morpholinium, piperidinium, 2-phenethylammonium, 2-methyl-benzylammonium, n-hexylammonium, triethylammonium, trimethylammonium, tri(n-butyl)ammonium, methoxyethylammonium, diisopropylammonium, pyridinium, diallylammonium, pyrazolium, propargylammonium, dimethylhydrazinium, hydroxyammonium, methoxyammonium, dodecylammonium, octadecylammonium, 4-dichlorophenylammonium, 4-nitrobenzylammonium, benzyltrimethyl-ammonium, 2-hydroxyethyldimethyloctadecylammonium, 2-hydroxyethyldiethyloctylammonium, decyltrimethylammonium, hexyltriethylammonium and 4-methylbenzyltrimethylammonium.

Preferably, the compounds of the invention are those of the formula

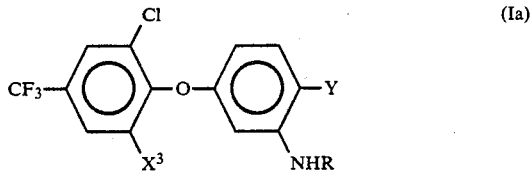

wherein

R is as defined above;

$X^3$ is a hydrogen atom, a chlorine atom, or a fluorine atom, most preferably a hydrogen atom;

Y is a nitro group, a chlorine atom, or a bromine atom;

$R^1$ and $R^2$, independently of each other and in each ($CHR^1$) and ($CHR^2$) group, are a hydrogen atom or an unsubstituted or substituted straight- or branched-chain ($C_1$–$C_6$) alkyl group;

A is —N($R^1$)— wherein $R^1$ is a hydrogen atom or an unsubstituted or substituted straight- or branched-chain ($C_1$–$C_6$) alkyl group, —O—, —S—, —C(O)—, or —C(O)B—;

B is —O—, —N($R^4$)—, or a straight- or branched-chain ($C_1$–$C_6$) alkylene group;

$R^3$ is a cyano group or a group of the formula —C(O)Z;

$R^4$ is a hydrogen atom or an unsubstituted or substituted straight- or branched-chain ($C_1$–$C_6$)alkyl group;

Z is —$OR^5$ or —N($R^4$)$SO_2R^5$;

$R^5$ is a hydrogen atom, an unsubstituted or substituted straight- or branched-chain ($C_1$–$C_6$) alkyl group, or an agronomically-acceptable alkaline earth metal cation, an alkali metal cation or an ammonium or substituted ammonium cation;

$R^6$ is an unsubstituted straight- or branched-chain ($C_1$–$C_6$) alkyl group;

m is 2 or 3; and n is 1.

More preferably, the compounds are those of formula (Ia) wherein $X^3$ is a hydrogen atom;

Y is a nitro group, a chlorine atom, or a bromine atom;

$R^1$ and $R^2$, independently of each other and in each ($CHR^1$) and ($CHR^2$) group, are a hydrogen atom or an unsubstituted or substituted straight- or branched-chain ($C_1$–$C_6$) alkyl group;

A is —O—, —N(H)—, —N($CH_3$)—, —N($CH_2OCH_3$)—, —S—, —C(O)—, or —C(O)B—;

B is —O— or a straight- or branched-chain ($C_1$–$C_6$) alkylene group;

$R^3$ is a cyano group or a group of the formula —C(O)Z;

Z is —$OR^5$;

$R^5$ is an unsubstituted or substituted straight- or branched-chain ($C_1$–$C_6$) alkyl group, or an alkaline earth metal, an alkali metal, or ammonium or substituted ammonium cation;

m is 2 or 3; and n is 1.

Still more preferably, the compounds are those of formula (Ia) wherein $X^3$ is a hydrogen atom;

Y is a nitro group, a chlorine atom, or a bromine atom;

$R^1$ and $R^2$, independently of each other and in each ($CHR^1$) and ($CHR^2$) group, are a hydrogen atom or an unsubstituted or substituted straight- or branched-chain ($C_1$-$C_6$) alkyl group;

A is —O—, —N(H)—, —S—, —C(O)—, or —C(O)B—;

B is —O—;

$R^3$ is a cyano group or a group of the formula —C(O)Z;

Z is -$OR^5$;

$R^5$ is a hydrogen atom, an unsubstituted or substituted straight- or branched-chain ($C_1$-$C_6$) alkyl group, or an alkaline earth metal, an alkali metal, or substituted ammonium cation;

m is 2 or 3; and n is 1.

Most preferably, the compounds are those of formula (Ia) wherein $X^3$ is a hydrogen atom;

Y is a nitro group or a chlorine atom;

$R^1$ and $R^2$, independently of each other and in each ($CHR^1$) and ($CHR^2$) group, are a hydrogen atom or an unsubstituted or substituted straight- or branched-chain ($C_1$-$C_6$) alkyl group;

A is —O—, —N(H)—, —S—, —C(O)—, or —C(O)B—;

B is —O—;

$R^3$ is a cyano group or a group of the formula —C(O)Z;

Z is —$OR^5$;

$R^5$ is a hydrogen atom; an unsubstituted or substituted straight- or branched-chain ($C_1$-$C_6$) alkyl group, or an alkali metal cation, preferably sodium or potassium, or an ammonium or substituted ammonium cation;

m is 2 or 3; and n is 1.

The compounds of the present invention can be made by a wide variety of conventional reaction procedures. For example, compounds of the present invention in which Y is a nitro group can be prepared by the following general procedure. To a solution of m-nitrophenol in a polar solvent, such as dimethylsulfoxide, dimethylformamide, sulfolane, dioxane, is added a base, such as potassium hydroxide, potassium carbonate, triethylamine, followed by a compound of the formula Q-Cl, wherein Q is as defined above. The mixture is allowed to stir at any temperature between about 25° and about 220°, depending on the solvent, preferably at about 100°-180°. Upon completion, the reaction mixture is diluted with water, extracted with an organic solvent, such as ether, methylene chloride, hexane, ethyl acetate, ethylene dichloride. The volatiles are removed under reduced pressure and the crude product is purified by distillation. The mononitro product above is dissolved in an organic solvent, such as methylene chloride, ethylene dichloride, and stirred vigorously with concentrated sulfuric acid. Potassium nitrate is added such that the internal temperature of the reaction is maintained between about −10° to 10° C. Upon completion of the reaction the product is purified as above and the final product was recrystallized from an appropriate solvent, such as ethanol, to yield a compound of the formula

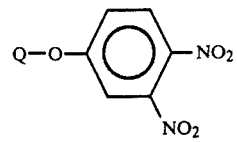

(II)

wherein Q is as defined above.

An amine of the formula $NH_2R$, wherein R is as defined above, is allowed to react with the compound of formula (II) in a polar solvent, such as dimethylsulfoxide, dioxane, dimethylformamide, sulfolane, ethanol, tetrahydrofuran, in the presence of base, such as the following potassium salts: carbonate, hydroxide, t-butoxide, or nitrogen bases, such as triethylamine or diisopropyl ethylamine, at between about −24° and 150° C., preferably 25°14 100° C. Upon completion, products purified as above and the final product were either recrystallized from the appropriate polar solvent or purified by column chromatography, to yield the desired diphenyl ether of the invention having the formula

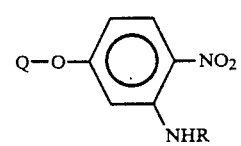

(III)

Free acids can be esterified using one of the following procedures: acid catalysts, such as hydrochloric acid or p-toluenesulfonic acid in an alcohol, such as methanol, ethanol, or isopropanol; treatment with base, such as potassium hydroxide, carbonate or hydride followed by an alkylating agent, such as iodomethane, isopropyl bromide; treatment with a chloroformate, such as methyl or ethyl chloroformate in the presence of an organic base, such as triethylamine or pyridine in an organic solvent, such as benzene, toluene.

In another procedure, when A is —O—, a compound of the formula

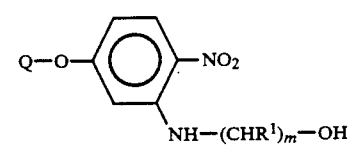

(IV)

wherein Q, $R^1$ and m are as defined above, and which has been prepared by the procedure described above with an amine of the formula $NH_2$—($CHR^1$)$_m$—OH, is dissolved in a suitable inert solvent and the solution is added to a suspension or solution of a suitable, conventional base, such as, for example, sodium hydride or hydroxide or alkoxide at temperatures ranging from about −10° C. to about 120° C., examples of said suitable inert solvent being tetrahydrofuran, dimethoxyethane, dimethylsulfoxide, and sulfolane, preferably tetrahydrofuran. An alkylating agent of the formula X—($CHR^2$)$_n$—$R^3$, wherein X is a halogen atom, preferably a bromine atom or other leaving group, and $R^2$, $R^3$ and n are as defined above, is added and the resulting mixture is stirred at a temperature of from about room temperature to reflux temperature. The reaction mixture is then diluted with water, extracted with an organic solvent, and the extracts are dried over a drying agent, such as, for example, magnesium sulfate, potassium carbonate, sodium sulfate, and molecular seives. Filtration of the drying agent and concentration of the organic filtrate by evaporating the solvent under reduced pressure affords the desired product.

Compounds of the present invention in which Y is a cyano group or a halogen atom can be prepared, for example, by the following general procedure. Following the procedure set forth above, a compound of the formula Q-Cl, wherein Q is as defined above, is reacted with a compound of the formula

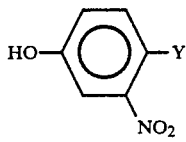

(V)

wherein Y is a cyano group or a halogen atom. The final product is then reduced using conventional techniques, for example, catalytic hydrogenation using a palladium or platinum or charcoal catalyst and a polar solvent, such as ethyl acetate, acetic acid or ethanol, and purified by column chromatography, to give a compound of the formula

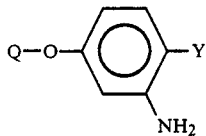

(VI)

wherein Q is as defined above and Y is a cyano group or a halogen atom.

The compound of formula (VI) is allowed to react with an appropriately-substituted electrophile, for example, a compound having the formula XR, wherein X is a halogen atom, preferably a bromine atom, or other leaving group, in a polar solvent in the presence of base. Upon completion of the reaction, the mixture is diluted with water, extracted with an organic solvent, such as ether, methylene chloride, ethyl acetate, and concentrated under reduced pressure to afford the crude product, which can be purified by column chromatography.

Compounds of the invention can also be made by appropriate post-reactions involving intermediates prepared by the procedures set forth above or by other conventional preparative techniques.

Typical compounds representative of the present invention include the following:

Methyl, ethyl, and sodium 2-(3-N-(5-(2-chloro-4-(trifluoromethyl)phenoxy)-2-nitrophenyl)aminopropoxy) acetate Methyl, ethyl, and sodium 2-(2-N-(5-(2-chloro-4-(trifluoromethyl)phenoxy)-2-nitrophenyl)aminoethoxy) acetate Methyl, ethyl, and sodium 2-(1-N-(5-(2-chloro-4-(trifluoromethyl)phenoxy)-2-nitrophenyl)aminoethoxy) propionate Methyl, ethyl, and sodium 2-(1-N-(5-(2-chloro-4-(trifluoromethyl)phenoxy)-2-nitrophenyl)aminoethoxy) acetate Methyl, ethyl, and sodium 2-(2-N-(5-(2-chloro-4-(trifluoromethyl)phenoxy)-2-nitrophenyl)aminopropoxy) acetate Methyl, ethyl, and sodium 2-(2-N-(5-(2-chloro-4-(trifluoromethyl)phenoxy)-2-nitrophenyl)aminoisopropoxy) acetate Methyl, ethyl, and sodium 2-(2-N-(5-(2-chloro-4-(trifluoromethyl)phenoxy)-2-nitrophenyl)aminoethoxy) propionate Methyl, ethyl, and sodium 2-(2-N-(5-(2-chloro-4-(trifluoromethyl)phenoxy)-2-nitrophenyl)aminoethylamino) acetate Methyl, ethyl, and sodium 2-(2-N-(5-(2-chloro-4-(trifluoromethyl)phenoxy)-2-nitrophenyl)aminothioisopropoxy) acetate Methyl, ethyl, and sodium 2-(3-N-(5-(2-chloro-4-(trifluoromethyl)phenoxy)-2-nitrophenyl)amino)propionate 1-(Methoxycarbonyl)-4-N-(5-(2-chloro-4-(trifluoromethyl) phenoxy)-2-nitrophenyl)amino)butanone, and corresponding ethyl ester and sodium salt 1-(Thiomethoxycarbonyl)-4-N-(5-(2-chloro-4-(trifluoromethyl) phenoxy)-2-nitrophenyl)amino)butanone, and corresponding ethyl ester and sodium salt 2-(2-N-(5-(2-chloro-4-(trifluoromethyl)phenoxy)-2-nitrophenyl)aminothioproposy)acetonitrile 3-(3-N-(5-(2-chloro-4-(trifluoromethyl)phenoxy)-2-nitrophenyl)aminopropoxy) propionitrile 3-(1-ethyl-3-N-(5-(2-chloro-4-(trifluoromethyl)-phenoxy)-2-nitrophenyl)aminopropylamino) propionitrile Methyl, ethyl, and sodium 2-(2-(1-cyano)-2-N-(5-(2-chloro-4-(trifluoromethyl)phenoxy)-2-nitrophenyl)aminoethoxy)acetate Methyl, ethyl, and sodium 2-(1-methoxy-2-N-(5-(2-chloro-4-(trifluoromethyl)phenoxy)-2-nitrophenyl) aminoethoxy)acetate Methyl, ethyl, and sodium 2-(2-methoxy methyl)-2-N-(5-(2-chloro-4-(trifluoromethyl) phenoxy)-2-nitrophenyl)aminoethoxy)acetate O-(2-N-(5-(2-chloro-4-(trifluoromethyl)-phenoxy)-2-nitrophenyl)aminoethyl) chloroethane O-(2-N-(5-(2-chloro-4-(trifluoromethyl)-phenoxy)-2-nitrophenyl)aminopropenyl) bromoethane Methoxymethyl 2-(2-N-(5-(2-chloro-4-(trifluoromethyl)phenoxy)-2-nitrophenyl)aminoethoxy)-acetate, and corresponding ethyl ester and sodium salt Methyl, ethyl, and sodium 2-(2-N-(5-(2-chloro-4-(trifluoromethyl)phenoxy)-2-bromophenyl)aminoethoxy) acetate Methyl, ethyl, and sodium 2-(2-N-(5-(2-chloro-4-(trifluoromethyl)phenoxy)-2-chlorophenyl)aminoethoxy) propionate Methyl, ethyl and sodium 2-(2-N-(5-(2,6-dichloro-4-(trifluoromethyl)phenoxy)-2-bromophenyl)aminoethoxy) acetate Methyl, ethyl, and sodium 2-(2-(5-(2-chloro-4-(trifluoromethyl)phenoxy)-2-cyanophenyl)aminopropoxy) acetate Methyl, ethyl, and sodium 2-(2-N-(5-(2-chloro-4-(trifluoromethyl)phenoxy)-2-chlorophenyl) aminoisopropoxy)acetate Methyl, ethyl, and sodium 2-(2-N-(5-(2,4-dichloro phenoxy)-2-nitrophenyl)aminoethoxy) acetate Methyl, ethyl, and sodium 2-(2-N-(5-(2-chloro-4-bromophenoxy)-2-nitrophenyl)aminoethoxy) propionate Methyl, ethyl and sodium 2-(2-N-(5-(2-cyano-4-(trifluoromethyl)phenoxy)-2-nitrophenyl)aminoethoxy) acetate Methyl, ethyl, and sodium 2-(2-N-(5-(2-chloro-4-cyanophenoxy)-2-nitrophenyl)aminopropoxy) acetate Methyl, ethyl, and sodium 2-(2-N-(5-(2,4-dichloro)-phenoxy)-2-bromophenyl)aminoisopropoxy) acetate Propyl, isopropyl, butyl, sec-butyl, tert-butyl, pentyl, and hexyl 2-(2-N-(5-(2-chloro-4-(trifluoromethyl)-phenoxy-2-chlorophenyl)aminoethoxy) propionate Methyl, ethyl, and sodium 2-(2-N-(5-(3-chloro-5-(trifluoromethyl)pyridyloxy)-2-nitrophenyl)aminoethoxy) acetate Methyl, ethyl, and sodium 2-(2-N-(5-(3-chloro-5-(trifluoromethyl)pyridyloxy)-2-nitrophenyl)aminopropoxy) acetate Methyl, ethyl, and sodium 2-(2-N-(5-(2-cyano-4-(trifluoromethyl)phenoxy)-2-nitrophenyl)aminoethoxy) acetate Propyl, isopropyl, butyl, sec-butyl, tert-butyl, isobutyl, pentyl, and hexyl 2-(2-N-(5-(2-chloro-4-(trifluoromethyl)phenoxy)-2-nitrophenyl)aminoethoxy) acetate Methyl, ethyl, and sodium 2-(2-N-(5-(2-chloro-4-(difluoroethyl)phenoxy)-2-nitrophenyl)aminoethoxy) acetate Methyl, ethyl, and sodium 2-(2-N-(5-(2-chloro-4-(difluorochloromethyl)phenoxy)-2-nitrophenyl) aminoethoxy) acetate Methyl, ethyl, and sodium 2-(2-N-(5-(2,6-dichloro-4-(trifluoromethyl)phenoxy)-2-nitrophenyl)aminoethoxy) acetate as well as the corresponding free acids of each of the foregoing compounds.

Preferred compounds of the present invention include the following:

1-(Methoxycarbonyl)-4-N-(5-(2-chloro-4-(trifluoromethyl) phenoxy)-2-nitrophenyl)amino)butanone Methyl 2-(2-N-(5-(2,4-dichloro phenoxy)-2-nitrophenyl)-aminoethoxy) acetate Methyl 2-(2-N-(5-(2-chloro-4-(trifluoromethyl)-phenoxy)-2-chlorophenyl)aminoethoxy) propionate Methyl 1-(2-N-(5-(2-chloro-4-(trifluoromethyl)-phenoxy)-2-bromophenyl)aminoethoxy) acetate Methyl 2-(2-N-(5-(2-chloro-4-(trifluoromethyl)-phenoxy)-2-cyanophenyl)aminopropoxy) acetate Methyl 2-(2-N-(5-(2-chloro-4-(trifluoromethyl)-phenoxy)-2-nitrophenyl)aminoethoxy) acetate Methyl 2-(2-N-(5-(2-chloro-4-(trifluoromethyl)-phenoxy)-2-nitrophenyl)aminopropoxy) acetate Methyl 2-(2-N-(5-(2-chloro-4-(trifluoromethyl)-phenoxy)-2-nitrophenyl)aminoisopropoxy) acetate Methyl 2-(3-N-(5-(2-chloro-4-(trifluoromethyl)-phenoxy)-2-nitrophenyl)aminopropoxy) acetate The ethyl esters and sodium salts of the above compounds, as well as the corresponding acids, are also among the preferred compounds of the present invention.

The most preferred compounds of the present invention include the following:

Methyl 2-(2-N-(5-(2-chloro-4-(trifluoromethyl)-phenoxy)-2-nitrophenyl)aminoethoxy) acetate Methyl 2-(2-N-(5-(2-chloro-4-(trifluoromethyl)-phenoxy)-2-nitrophenyl)aminopropoxy) acetate Methyl 2-(2-N-(5-(2-chloro-4-(trifluoromethyl)-phenoxy)-2-nitrophenyl)aminoisopropoxy) acetate Methyl 2-(3-N-(5-(2-chloro-4-(trifluoromethyl)-phenoxy)-2-nitrophenyl)aminopropoxy) acetate Methyl 2-(3-N-(5-(2-chloro-4-(trifluoromethyl)-phenoxy)-2-nitrophenyl)aminobutoxy) acetate Methyl 2-(3-N-(5-(2-chloro-4-(trifluoromethyl)-phenoxy)-2-nitrophenyl)aminobutoxy) propionate Further examples of compounds of the present invention (some of which are also named above) include those of formula (Ia) in which $X^3$ is a hydrogen atom, Y is a nitro group or a chlorine atom, and NHR is $NHCH_2CH_2CH_2OCH_2CO_2CH_3$
$NHCH(CH_3)CH_2CH_2OCH_2CO_2CH_3$
$NHCH_2CH_2CH_2CH_2OCH_2CO_2CH_3$
$NHCH(CH_3)CH_2CH_2CH_2OCH_2CO_2CH_3$
$NHCH_2CH_2CH_2CH_2OCH_2CO_2CH_3$
$NHCH(CH_3)CH_2CH_2CH_2OCO_2CH_3$
$NHCH_2CH_2OCH_2CH_2OCH_2CO_2CH_3$ $NHCH_2CH_2SCH_2CO_2CH_3$
$NHCH(CH_3)CH_2SCH_2CO_2CH_3$
$NHCH_2CH_2CH_2SCH_2CO_2CH_3$
$NHCH(CH_3)CH_2CH_2SCH_2CO_2CH_3$
$NHCH_2CH_2CH_2CH_2SCH_2CO_2CH_3$
$NHCH(CH_3)CH_2CH_2CH_2SCH_2CO_2CH_3$ $NHCH_2CH_2NHCH_2CO_2CH_3$
$NHCH_2CH_2NHCH_2CH_2CO_2CH_3$
$NHCH_2CH_2N(CH_3)CH_2CO_2CH_3$
$NHCH_2CH_2N(CH_2OCH_3)CH_2CO_2CH_3$
$NHCH(CH_3)CH_2NHCH_2CO_2CH_3$
$NHCH_2CH_2CH_2NHCH_2CO_2CH_3$
$NHCH(CH_3)CH_2CH_2NHCH_2CO_2CH_3$
$NHCH_2CH_2NHSO_2CH_2CO_2CH_3$
$NHCH_2CH_2N(CH_3)SO_2CH_2CO_2CH_3$
$NHCH_2CH_2COCH_2CO_2CH_3$
$NHCH(CH_3)CH_2COCH_2CO_2CH_3$ as well as the isomers of the above compounds in which the position of the side-chain methyl group is varied, compounds corresponding to the above compounds in which —S— is replaced by —S(O)— or by —S(O)$_2$— and the ethyl esters, sodium salts, and free acids of each of the above compounds.

The novel diphenyl ethers of the invention are useful both as preemergence and as postemergence herbicides. Preemergence herbicides are ordinarily used to treat the soil in which the desired crop is to be planted by application either before seeding, during seeding, or, as in most applications, after seeding and before the crop emerges. Postemergence herbicides are those which are applied after the weed plants have emerged and during their growth period.

Among the crops on which diphenyl ethers of the invention can be advantageously employed are, for example, cotton, soybeans, peanuts, safflower, beans, rice, peas, carrots, corn, wheat and other cereal crops.

The diphenyl ethers of the invention can be applied in any amount which will give the required control of weeds. A preferred rate of application of the herbicides of the invention is from about 0.01 to about 12, and most preferably about 0.1 to about 4 pounds of the diphenyl ether per acre.

Under some conditions, the diphenyl ethers of the invention may be advantageously incorporated into the soil or other growth medium prior to planting a crop. This incorporation can be carried out by any convenient means, including by simple mixing with the soil, by applying the diphenyl ether to the surface of the soil and then disking or dragging into the soil to the desired depth, or by employing a liquid carrier to accomplish the necessary penetration and impregnation.

When used in transplanted rice crops, diphenyl ethers of the invention can be applied either preemergence or postemergence to the weeds—that is, they can be applied to the growth medium of the transplanted plants either before the weed plants have emerged or while they are in their early stages of growth. The ethers can be applied to the growth medium either before or after the rice has been transplanted to that medium.

A diphenyl ether of the invention can be applied to the growth medium or to plants to be treated either by itself or, as is generally done, as a component in a herbicidal composition or formulation which also comprises an agronomically-acceptable carrier. By agronomically-acceptable carrier is meant any substance which can be used to dissolve, disperse, or diffuse a herbicidal compound in the composition without impairing the effectiveness of the herbicidal compound and which by itself has no detrimental effect on the soil, equipment, crops, or agronomic environment. Mixtures of the diphenyl ethers of the invention may also be used in any of these herbicidal formulations. The herbicidal compositions of the invention can be either solid or liquid formulations or solutions. For example, diphenyl ethers of the invention can be formulated as solutions, wettable powders, emulsifiable concentrates, dusts, granular formulations, aerosols, or flowable emulsion concentrates. In such formulations, the compounds are extended with a liquid or solid carrier and, when desired, suitable surfactants are incorporated.

It is usually desirable, particularly in postemergence applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The diphenyl ether compounds of this invention can be dissolved in any appropriate solvent. Examples of solvents which are useful in the practice of this invention include water, alcohols, ketones, halogenated hydrocarbons, dimethylformamide, dioxane, dimethyl sulfoxide, and the like. Mixtures of these solvents can also be used. Aromatic hydrocarbons can be added to the solvent to enhance the solubility of the diphenyl ether in the solvent. The concentration of the solution can vary from about 2% to about 98% with a preferred range being about 25% to about 75%.

For the preparation of emulsifiable concentrates, the diphenyl ether can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as the alkaline earth salts or ammonium salts of sulfates and sulfonates, alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent, such as a water-soluble cellulose derivative or a water-soluble salt of a polyacrylic acid. The concentration of the active ingredient in emulsifiable concentrates is usually about 10% to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent can constitute about 0.5% to about 3% of the composition, and a wetting agent can constitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable power with a finely divided carrier. Dust concentrates containing about 20% to 80% of the active ingredient are commonly made and are subsequently diluted to about 1% to 10% use concentration.

Granular formulations can be prepared by impregnating a solid, such as granular fuller's earth, vermiculite, ground corn cobs, seed hulls, including bran or other grain-hulls, or similar material. A solution of one or more of the diphenyl ethers in a volatile organic solvent can be sprayed or mixed with the granular solid and the solvent then removed by evaporation. The granular material can have any suitable size, with a preferable size range of 16 to 60 mesh. The diphenyl ether will usually comprise about 2 to 15% of the granular formulation.

The diphenyl ethers of the invention can also be mixed with fertilizers or fertilizing materials before their application. In one type of solid fertilizing composition in which the diphenyl ethers can be used, particles of a fertilizer or fertilizing ingredients, such as ammonium sulfate, ammonium nitrate, or ammonium phosphate, can be coated with one or more of the ethers. The solid diphenyl ethers and solid fertilizing material can also be admixed in mixing or blending equipment, or they can be incorporated with fertilizers in granular formations. Any relative proportion of diphenyl ether and fertilizer can be used which is suitable for the crops and weeds to be treated. The diphenyl ether will commonly be from about 5% to about 25% of the fertilizing composition. These compositions provide fertilizing materials which promote the rapid growth of desired plants, and at the same time control the growth of undesired plants.

The diphenyl ethers of the invention can be applied as herbicidal sprays by methods commonly employed, such as conventional high-gallonage hydraulic sprays, low gallonage sprays, airblast spray, aerial sprays and dusts. For low volume applications a solution of the compound is usually used. The dilution and rate of application will usually depend upon such factors as the type of equipment employed, the method of application, the area to be treated and the type and stage of development of the weeds.

For some applications, it may be desirable to add one or more other herbicides along with diphenyl ethers of the invention. Examples of other herbicides which can be incorporated to provide additional advantages and effectiveness include:

Carboxylic Acids And Derivatives 2,3,6-trichlorobenzoic acid and its salts
2,3,5,6-tetrachlorobenzoic acid and its salts
2-methoxy-3,5,6-trichlorobenzoic acid and its salts
2-methoxy-3,6-dichlorobenzoic acid and its salts
2-methyl-3,6-dichlorobenzoic acid and its salts
2,3-dichloro-6-methylbenzoic acid and its salts
2,4-dichlorophenoxyacetic acid and its salts and esters
2,4,5-trichlorophenoxyacetic acid and its salts and esters
2-methyl-4-chlorophenoxyacetic acid and its salts and esters
2-(2,4,5-trichlorophenoxy)propionic acid and its salts and esters
4-(2,4-dichlorophenoxy)butyric acid and its salts and esters
4-(2-methyl-4-chlorophenoxy)butyric acid and its salts and esters
2,3,6-trichlorophenylacetic acid and its salts
3,7-endoxohexahydrophthalic acid
Dimethyl 2,3,5,6-tetrachloroterephthalate
Trichloroacetic acid and its salts
2,2-dichloropropionic acid and its salts
2,3-dichloroisobutyric acid and its salts

Carbamic Acid Derivatives

Ethyl N,N-di(n-propyl)thiolcarbamate
Propyl N,N-di(n-propyl)thiolcarbamate
Ethyl N-ethyl-N-(n-butyl)thiolcarbamate
Propyl N-ethyl-N-(n-butyl)thiolcarbamate
2-chloroallyl N,N-diethyldithiocarbamate
N-methyldithiocarbamic acid salts
Ethyl 1-hexamethyleneiminebarbothiolate
Isopropyl N-phenylcarbamate
Isopropyl N-(m-chlorophenyl)carbamate
4-chloro-2-butynyl N-(m-chlorophenyl)carbamate
Methyl N-(3,4-dichlorophenyl)carbamate

Phenols

Dinitro-o-(sec-butyl)phenol and its salts
Pentachlorophenol and its salts

Substituted Ureas 3-(3,4-dichlorophenyl)-1,1-dimethylurea
3-phenyl-1,1-dimethylurea
3-(3,4-dichlorophenyl)-3-methoxy-1,1-dimethylurea
3-(4-chlorophenyl)-3-methoxy-1,1-dimethylurea
3-(3,4-dichlorophenyl)-2-n-butyl-1-methylurea
3-(3,4-dichlorophenyl)-1-methoxy-1-methylurea
3-(4-chlorophenyl)-1-methoxy-1-methylurea
3-(3,4-dichlorophenyl)-1,1,3-trimethylurea
3-(3,4-dichlorophenyl)-1,1-diethylurea
Dichloral urea

Substituted Triazines 2-chloro-4,6-bis(ethylamino)-2-triazine
2-chloro-4-ethylamino-6-isopropylamino-s-triazine
2-chloro-4,6-bis(methoxypropylamino)-2-triazine
2-methoxy-4,6-bis(isopropylamino)-s-triazine
2-chloro-4-ethylamino-6-(3-methoxypropylamino)-s-triazine
2-methylmercapto-4,6-bis(isopropylamino)-s-triazine
2-methylmercapto-4,6-bis(ethylamino)-s-triazine
2-methylmercapto-4-ethylamino-6-isopropylamino-s-triazine
2-chloro-4,6-bis(isopropylamino)-s-triazine
2-methoxy-4,6-bis(ethylamino)-s-triazine
2-methoxy-4-ethylamino-6-isopropylamino-s-triazine
2-methylmercapto-4-(2-methoxyethylamino)-6-isopropyl-amino-s-triazine

Diphenyl Ether Derivatives 2,4-dichloro-4'-nitrodiphenyl ether
2,4,6-trichloro-4'-nitrodiphenyl ether
2,4-dichloro-6-fluoro-4'-nitrodiphenyl ether
3-methyl-4'-nitrodiphenyl ether
3,5-dimethyl-4'-nitrodiphenyl ether
2,4'-dinitro-4-trifluoromethyldiphenyl ether
2,4-dichloro-3'-methoxy-4'-nitrodiphenyl ether
2-chloro-4-trifluoromethyl-3'-[2-(methoxycarbonyl)-ethoxycarbonyl]-4'-nitro diphenyl ether
2-chloro-4-trifluoromethyl-3'-[1-(methoxycarbonyl)-ethoxycarbonyl]-4'-nitrodiphenyl ether
2-chloro-4-trifluoromethyl-3'-[(ethoxycarbonyl)methoxycarbonyl]-4'-nitrodiphenyl ether
5-(2-chloro-4-trifluoromethylphenoxy)-2-nitro-N-methanesulfonyl benzamide
Sodium 5-(2-chloro-4-(trifluoromethyl)phenoxy)-2-nitrobenzoate
2-chloro-1-(3-ethoxy-4-nitrophenoxy)-4-(trifluoromethyl)benzene
Ethyl 5-(2-chloro-4-(trifluoromethyl)phenoxy)-2-nitrobenzoate
Methyl 5-(2-chloro-4-(trifluoromethyl)phenoxy)-2-nitrobenzoate
2-chloro-4-trifluoromethyl-3'-[1-(ethoxycarbonyl)-ethoxycarbonyl]-4'-nitrodiphenyl ether

Anilides

N-(3,4-dichlorophenyl)propionamide
N-(3,4-dichlorophenyl)methacrylamide
N-(3-chloro-4-methylphenyl)-2-methylpentanamide
N-(3,4-dichlorophenyl)trimethylacetamide
N-(3,4-dichlorophenyl)-alpha,alpha,-dimethylvaleramide
N-isopropyl-N-phenylchloroacetamide
N-n-butoxymethyl-N-(2,6-diethylphenyl)-chloroacetamide
N-n-methoxymethyl-N-(2,6-diethylphenyl)-chloroacetamide

Uracils 5-bromo-3-s-butyl-6-methyluracil
5-bromo-3-cyclohexyl-1,6-dimethyluracil
3-cyclohexyl-5,6-trimethyleneuracil
5-bromo-3-isopropyl-6-methyluracil
3-tert-butyl-5-chloro-6-methyluracil

Nitriles 2,6-dichlorobenzonitrile
Diphenylacetonitrile
3,5-dibromo-4-hydroxybenzonitrile
3,5-diiodo-4-hydroxybenzonitrile

Other Organic Herbicides 2-chloro-N,N-diallylacetamide
N-(1,1-dimethyl-2-propynyl)-3,5-dichlorobenzamide
maleic hydrazide
3-amino-1,3,4-triazole monosodium methanearsonate
disodium methanearsonate
N,N-dimethyl-alpha,alpha-diphenylacetamide
N,N-di(n-propyl)-2,6-dinitro-4-trifluoromethylaniline
N,N-di(n-propyl)-2,6-dinitro-4-methylaniline
N,N-di(n-propyl)-2,6-dinitro-4-methylsulfonylaniline O-(2,4-dichlorophenyl)-O-methyl-isopropylphosphoramido-thioate 4-amino-3,5,6-trichloropicolinic acid 2,3-dichloro-1,4-naphthoquinone-di(methoxy-thiocarbonyl) disulfide 3-isopropyl-1H-2,1,3-benzothiadiazin-(4)3H-one-2,2-dioxide 6,7-dihydrodipyridol[1,2-a:2',1'-c]pyrazidinium salts 1,1'-dimethyl-4,4'-bipyridinium salts 3,4,5,6-tetrahydro-3,5-dimethyl-2-thio-2H-1,3,5-thiadiazine 2-chloro-N-[(4-methoxy-6-methyl-1,3,5-triazin-2-yl)amino carbonyl]benzene sulfonamide 2-(1-allyloxyamino-butylidine)-4-carbomethoxy-5-dimethyl-cyclohexan-1,3-dione 2-(1-ethoxyamino-butylidine)-5-(2-ethylsulfinyl-propyl)-cyclohexan-1,3-dione Butyl-2-[4-(5-trifluoromethyl-2-pyridyloxy)-phenoxy]propionate.

When mixtures of herbicides are employed, the relative proportions which are used will depend upon the crop to be treated and the degree of selectivity in weed control which is desired.

The following examples are illustrative of the present invention but are not intended to be construed as limiting the invention in scope. All parts and percentages are by weight unless otherwise indicated. The following Compound Nos. 1, 2, and 3 are represented by formula (VII) below.

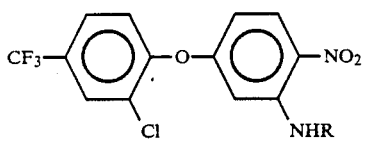

(VII)

Compound No. 1

Methyl 2-(2-N-(5-(2-chloro-4-(trifluoromethyl)-phenoxy)-2-nitrophenyl) aminoethoxy)acetate Compound No. 2

Methyl 2-(2-N-(5-(2-chloro-4-(trifluoromethyl)-phenoxy)-2-nitrophenyl) aminoethoxy)propionate Compound No. 3

Methoxycarbonylmethyl 3-N-(5-(2-chloro-4-(trifluoromethyl)-phenoxy)-2-nitrophenyl) amino)propionate Preparation of Compound No. 1

To a suspension of sodium hydride (1.2 equivalents) in tetrahydrofuran at 10° C. was added a solution of 2-N-(5-(2-chloro-4-(trifluoromethyl) phenoxy)-2-nitrophenyl)aminoethanol (1 equivalent). After the evolution of hydrogen ceased, methyl bromoacetate (two equivalents) was added. The final mixture was concentrated under reduced pressure, dissolved in ether, shaken with brine and dried oven magnesium sulfate. Filtration and evaporation yielded Compound No. 1, mp 77°–78° C.

By following substantially the same procedure set forth in the description of the preparation of Compound No. 1, except for replacing the methyl bromopropionate, Compound No. 2 was produced. Compound No. 3 was produced by alkylating (3-N-(5-(2-chloro-4-(trifluoromethyl)phenoxy)-2-nitrophenyl)aminopropionic acid with methyl bromoacetate using conventional alkylating reaction procedures.

The nmr data for Compound Nos. 1, 2, and 3 are listed in TABLE 1 and the elemental analytical data for Compound Nos. 1 and 3 are listed in TABLE 2 as follows:

TABLE 1

| Compound No. | R | NMR |
| --- | --- | --- |
| 1 | CH$_2$CH$_2$OCH$_2$CO$_2$CH$_3$ | 8.7–6.1(m,7); 4.2(s,2); 3.9(m,5); 3.5(m,2) |
| 2 | CH$_2$CH$_2$OCH(CH$_3$)CO$_2$CH$_3$ | 8.7–6.1(m,7); 3.8(m,8); 1.5(d,3) |
| 3 | CH$_2$CH$_2$CO$_2$CH$_2$CO$_2$CH$_3$ | 8.7–6.2(m,7); 4.7(s,2); 3.8(m,5); 2.9(t,2) |

TABLE 2

| Compound No. | Melting Point (°C.) | Composition | Element | Calculated | Found |
| --- | --- | --- | --- | --- | --- |
| 1 | 77–78° | C$_{18}$H$_{16}$ClF$_3$N$_2$O$_6$ | C | 48.2 | 47.99 |
|  |  |  | H | 3.6 | 3.53 |
|  |  |  | N | 6.2 | 6.17 |
|  |  |  | Cl | 7.9 | 8.01 |
|  |  |  | F | 12.7 | 12.45 |
| 3 | 60–61° | C$_{19}$H$_{16}$ClF$_3$N$_2$O$_7$ | C | 47.8 | 48.15 |
|  |  |  | H | 3.4 | 4.05 |
|  |  |  | N | 5.9 | 5.70 |
|  |  |  | Cl | 7.4 | 6.68 |
|  |  |  | F | 12.0 | 10.43 |

Listed in TABLE 3 are the results of the primary herbicide screen for the three diphenylethers in TABLE 1. The scale is based on 0 to 100; O=no control, 100=100% control (complete kill).

The following test procedure was employed. Seeds of selected crops and weeds were planted in soil in flats. For preemergence tests, the flats were treated with the test compound immediately after the planting. For postemergence tests, the seeds were allowed to germinate, and after two weeks the flats are treated with the test compound. The compound to be evaluated was dissolved in acetone, diluted with water, and sprayed over the flats using a carrier volume equivalent to 50 gallons per acre at the rate of application (pounds per acre, lbs./A.) specified in the tables. About two weeks after the application of the test compound, the state of growth of the plants was observed and the phytotoxic effect of the compound was evaluated.

The following abbreviations are used in TABLE 3;

PRE = preemergence
POST = postemergence
CLK = cocklebur
MA = marigold
MG = morningglory
SIC = sicklepod
TOM = tomato
VEL = velvetleaf
BYG = barnyardgrass
DB = downy brome
FOX = foxtail
JON = Johnsongrass
NUT = nutsedge
WO = wild oats

TABLE 3

| Cmpd. No. | RATE (#/A) | TYPE REST | CKL | MA | MG | SIC | TOM | VEL | BYG | DB | FOX | JON | NUT | WO |
|---|---|---|---|---|---|---|---|---|---|---|---|---|---|---|
| 1 | 2 | PRE | 100 | 100 | 100 | 100 | 100 | 100 | 77 | 100 | 100 | 95 | 10 | 60 |
|  | 2 | POST | 100 | 100 | 100 | 100 | 100 | 100 | 28 | 15 | 65 | 35 | 10 | 25 |
|  | .5 | PRE | 85 | 100 | 100 | 100 | 100 | 100 | 30 | 35 | 100 | 15 | 0 | 10 |
|  | .5 | POST | 100 | 100 | 100 | 100 | 100 | 100 | 23 | 10 | 65 | 20 | 5 | 20 |
| 2 | .5 | PRE | 82 | 100 | 90 | 100 | 100 | 100 | 41 | 15 | 100 | 5 | 100 | 15 |
|  | .5 | POST | 93 | 100 | 65 | 95 | 100 | 100 | 14 | 20 | 0 | 15 | 15 | 20 |
|  | .1 | PRE | 14 | 10 | 10 | 0 | 10 | 55 | 6 | 0 | 25 | 0 | 10 | 0 |
|  | .1 | POST | 81 | 100 | 55 | 55 | 100 | 90 | 8 | 15 | 0 | 10 | 0 | 15 |
| 3 | 2 | PRE | 83 | 100 | 100 | 80 | 100 | 100 | 39 | 45 | 100 | 15 | 0 | 10 |
|  | 2 | POST | 98 | 100 | 100 | 90 | 100 | 100 | 17 | 25 | 30 | 15 | 10 | 5 |
|  | .5 | PRE | 68 | 100 | 100 | 10 | 100 | 100 | 24 | 35 | 95 | 0 | 0 | 5 |
|  | .5 | POST | 94 | 100 | 100 | 65 | 100 | 100 | 8 | 0 | 15 | 10 | 5 | 5 |

What is claimed is:

1. A compound having the formula

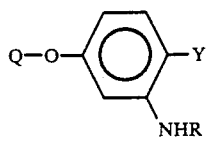

wherein:
Q is a group of the formula

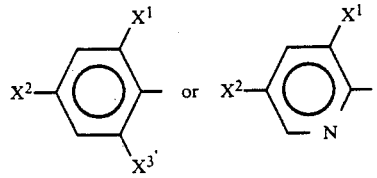

$X^1$ is a hydrogen atom, a cyano group, or a halogen atom;
$X^2$ is a haloalkyl group or a halogen atom;
$X^3$ is a hydrogen atom or a halogen atom;
Y is a nitro group, a cyano group, or a halogen atom;
R is a group of the formula

$R^1$ and $R^2$, independently of each other and in each $(CHR^1)$ and $(CHR^2)$ group, are a hydrogen atom, an unsubstituted or substituted straight- or branched-chain ($C_1$–$C_6$) alkyl group, a ($C_1$–$C_6$) alkoxy group, or a ($C_1$–$C_6$) alkylthio group, provided that $R^1$ and $R^2$ may not be alkoxy or alkylthio alpha to an —NH— moiety;
A is —N($R^1$)—, —N(O)—, —O—, —S—, —S(O)—, —S(O)$_2$—, —C(O)—, —C(O)B—, or —N(H)-S(O)$_2$—;
B is a straight- or branched-chain ($C_1$–$C_6$) alkylene group, —O—, —S—, or —N($R^4$)—;
$R^3$ is a cyano group, a halogen atom, or a group of the formula —C(O)Z;
$R^4$ is a hydrogen atom or an unsubstituted or substituted straight- or branched-chain ($C_1$–$C_6$) alkyl group;
Z is a hydrogen atom; an unsubstituted or substituted straight- or branched chain ($C_1$–$C_6$) alkyl group, —N($R^4$)$_2$, —OR$^5$, —SR$^5$, or —N($R^4$)SO$_2R^6$;
$R^5$ is a hydrogen atom, an unsubstituted or substituted straight- or branched-chain ($C_1$–$C_6$) alkyl group, or an agronomically-acceptable cation;
$R^6$ is an unsubstituted straight- or branched-chain ($C_1$–$C_6$) alkyl group, an unsubstituted or substituted phenyl group with up to three substituents which can be the same or different and are selected from chlorine, bromine, fluorine, ($C_1$–$C_6$) alkoxy and ($C_1$–$C_6$) alkyl which can be straight- or branched-chain and unsubstituted or substituted with up to three substituents which can be the same or different and are selected from chlorine, bromine, and ($C_1$–$C_6$) alkoxy, or a hydroxy group and its agronomically-acceptable salts;
m is an integer from 2 to 10; and
n is an integer from 1 to 3; and wherein
when $R^1$, $R^2$, $R^4$, or $R^5$ is a substituted alkyl group, there can be up to three substituents which can be the same or different and are selected from chlorine, bromine, fluorine, hydroxy, ($C_1$–$C_6$) alkoxy, ($C_1$–$C_6$) alkylthio, ($C_1$–$C_6$) aklylcarbonyl, ($C_1$–$C_6$) alkoxycarbonyl, amino, mono- or di-($C_1$–$C_6$) alkylamino, ($C_1$–$C_6$) alkylcarbonyloxy and unsubstituted or substituted phenyl, phenoxy, or phenylthio having up to three substituents which can be the same or different and are selected from chlorine, bromine, fluorine, hydroxy, ($C_1$–$C_6$) alkoxy, ($C_1$–$C_6$) alkylthio and ($C_1$–$C_6$) alkyl unsubstituted or substituted with up to three substituents which can be the same or different and are selected from chlorine, bromine, fluorine, hydroxy and ($C_1$–$C_6$) alkoxy.

2. A compound according to claim 1 wherein Q is a group of the formula

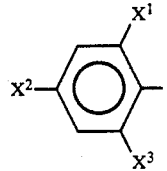

$X^1$ is a hydrogen atom, a chlorine atom, or a fluorine atom;
$X^2$ is a trifluoromethyl group;
$X^3$ is a hydrogen atom;
Y is a nitro group, a chlorine atom, or a bromine atom;
$R^1$ and $R^2$, independently of each other and in each $(CHR^1)$ and $(CHR^2)$ group, are a hydrogen atom or an unsubstituted or substituted straight- or branched-chain $C_1$–$C_6$ alkyl group;
A is —N($R^1$)—, —O—, —S—, —C(O)—, or —C(O)B—;

B is —O—, —N(R⁴)—, or a straight- or branched-chain (C₁-C₆)alkylene group;

R⁴ is a hydrogen atom or an unsubstituted or substituted straight- or branched-chain (C₁-C₆) alkyl group;

Z is —OR⁵ or —N(R⁴)SO₂R⁶;

R⁵ is an unsubstituted or substituted straight- or branched-chain (C₁-C₆) alkyl group, a hydrogen atom, or an agronomically-acceptable alkaline earth metal, an alkali metal, or ammonium or substituted ammonium cation;

R⁶ is unsubstituted straight- or branched-chain (C₁-C₆) alkyl group;

m is 2 or 3; and n is 1.

3. A compound according to claim 2 wherein:
A is —N(H)—, —N(CH₃)—, —N(CH₂OCH₃)—, —O—, —S—, —C(O)—, or —C(O)B—;
B is —O— or a straight- or branched-chain (C₁-C₆) alkylene group; and
Z is OR⁵.

4. A compound according to claim 3 wherein:
A is —N(H)—, —O—, —S—, —C(O)—, or —C(O)B—; and
B is —O—.

5. A compound according to claim 4 wherein:
R⁵ is a hydrogen atom, an unsubstituted or substituted straight- or branched-chain (C₁-C₆) alkyl group or a sodium, potassium, ammonium, or mono-, di-, tri- or tetraalkylammonium cation.

6. A compound according to claim 5 wherein:
R¹ and R², independently of each other and in each (CHR¹) and (CHR²) group, are a hydrogen atom or a methyl group;
A is —O—;
R³ is —C(O)Z;
R⁵ is a methyl group;
m is 2 or 3; and
n is 1.

7. A compound according to claim 6 having the formula:

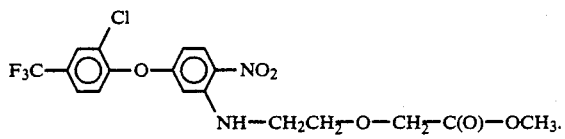

8. A compound according to claim 6 having the formula:

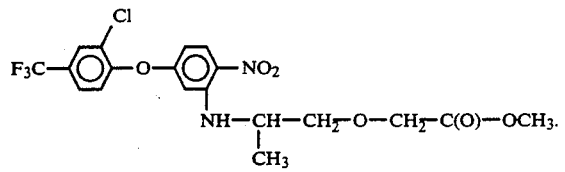

9. A compound according to claim 6 having the formula:

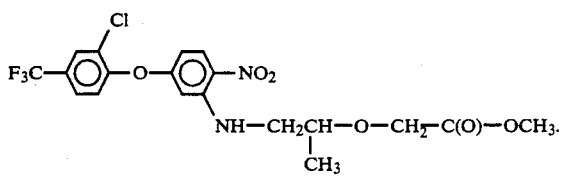

10. A compound according to claim 5 wherein:
Y is a nitro group or a chlorine atom;
R¹ and R² are each a hydrogen atom;
A is —N(H)—;
R³ is —C(O)Z;
Z is —OR⁵;
R⁵ is a methyl group;
m is 2 or 3; and
n is 1.

11. A compound according to claim 5 wherein:
Y is a nitro group or a chlorine atom;
R¹ and R², independently of each other and in each (CHR¹) and (CHR²) group, are a hydrogen atom or a methyl group;
A is —S—;
R³ is a cyano group or a group of the formula C(O)Z;
Z is —OR⁵;
R⁵ is a methyl group;
m is 2 or 3; and
n is 1.

12. A compound according to claim 5 wherein:
Y is a nitro group or a chlorine atom;
R¹ and R² are each a hydrogen atom;
A is —C(O)—;
R³ is —C(O)Z;
Z is —OR⁵;
R⁵ is a methyl group;
m is 2 or 3; and
n is 1.

13. A compound according to claim 5 wherein:
Y is a nitro group or a chlorine atom;
R¹ and R² are each a hydrogen atom;
A is —C(O)B—;
B is —O—;
R³ is —C(O)Z;
Z is —OR⁵;
R⁵ is a methyl group;
m is 2 or 3; and
n is 1.

14. A herbicidal composition comprising a herbicidally-effective amount of a compound according to claim 1 and an agronomically-acceptable carrier.

15. A method of controlling weeds which comprises applying to weed seedlings in a growth medium or to the growth medium prior to the emergence of the weeds therefrom a compound according to claim 1 in an amount sufficient to control the growth of the weeds.

16. A compound according to claim 1 wherein:
R³ is a cyano group or a group having the formula —C(O)Z, provided that when R³ is cyano, B is a straight- or branched-chain (C₁-C₆) alkylene group or —N(R⁴)—; and
Z is a hydrogen atom, an unsubstituted or substituted (C₁-C₆) alkyl group, —N(R⁴)₂, —OR⁵, or —N(R⁴)SO₂R⁶, provided that when Z is hydrogen, A is not —N(R¹)— or —N(H)S(O)₂— and B is not —N(R⁴)—.

17. A method of controlling weeds which comprises applying to weed seedlings in a growth medium or to the growth medium prior to the emergence of weeds therefrom a compound according to claim 16 in an amount sufficient to control the growth of the weeds.

18. A method as claimed in claim 15 wherein the growth medium contains seeds or growing plants capable of yielding an agronomic crop or said compound is applied prior to, or at the same time, as the planting of seeds or plants of an agronomic crop.

19. A method as claimed in claim 17 wherein the growth medium contains seeds or growing plants capable of yielding an agronomic crop or said compound is applied prior to, or at the same time as, the planting of seeds or plants of an agronomic crop.

* * * * *

UNITED STATES PATENT AND TRADEMARK OFFICE
CERTIFICATE OF CORRECTION

PATENT NO.    :   5,028,732

DATED         :   July 2, 1991

INVENTOR(S)   :   Ann H. Beaulieu, Roy Y. Yih

It is certified that error appears in the above-identified patent and that said Letters Patent is hereby corrected as shown below:

Column 18, line 46:  Delete "Claim 1", insert therefore --Claim 16.--

Column 20, line 50:  following "-$OR^5$" insert -- -$SR^5$--.

Signed and Sealed this

Second Day of February, 1993

*Attest:*

STEPHEN G. KUNIN

*Attesting Officer*    Acting Commissioner of Patents and Trademarks